US012741061B2

(12) United States Patent
Rizzi et al.

(10) Patent No.: US 12,741,061 B2
(45) Date of Patent: Sep. 22, 2026

(54) METHOD FOR OBTAINING HEALTHY INTESTINAL ORGANOIDS

(71) Applicant: PRECISION CANCER TECHNOLOGIES INC., Toronto (CA)

(72) Inventors: Simone Rizzi, Ecublens (CH); Jeremy Touati, Sottens (CH); Giulia Fregni, Nyon (CH); Cara Buchanan Pisano, Préverenges (CH); Franck Coumailleau, Lausanne (CH); Mathieu Heulot, Penthalaz (CH)

(73) Assignee: PRECISION CANCER TECHNOLOGIES INC., Toronto (CA)

( * ) Notice: Subject to any disclaimer, the term of this patent is extended or adjusted under 35 U.S.C. 154(b) by 317 days.

(21) Appl. No.: 17/640,681

(22) PCT Filed: Aug. 24, 2020

(86) PCT No.: PCT/EP2020/073586

§ 371 (c)(1),
(2) Date: Mar. 4, 2022

(87) PCT Pub. No.: WO2021/043606

PCT Pub. Date: Mar. 11, 2021

(65) Prior Publication Data

US 2022/0296784 A1 Sep. 22, 2022

(30) Foreign Application Priority Data

Sep. 6, 2019 (EP) .................................... 19195855

(51) Int. Cl.

| | |
|---|---|
| ***A61L 27/52*** | (2006.01) |
| ***A61L 27/38*** | (2006.01) |
| ***A61L 27/54*** | (2006.01) |
| ***C12N 5/00*** | (2006.01) |
| ***C12N 5/071*** | (2010.01) |

(52) U.S. Cl.

CPC ........... *A61L 27/52* (2013.01); *A61L 27/3804* (2013.01); *A61L 27/3882* (2013.01); *A61L 27/54* (2013.01); *C12N 5/0068* (2013.01); *C12N 5/0679* (2013.01); *A61L 2300/252* (2013.01); *C12N 2501/415* (2013.01); *C12N 2533/52* (2013.01)

(58) Field of Classification Search

None

See application file for complete search history.

(56) References Cited

U.S. PATENT DOCUMENTS

| | | | | |
|---|---|---|---|---|
| 2014/0193474 | A1* | 7/2014 | Babcock | A61L 29/14 428/476.3 |
| 2016/0279283 | A1* | 9/2016 | Griffin | A61L 27/58 |
| 2018/0258403 | A1 | 9/2018 | Lutolf et al. | |

FOREIGN PATENT DOCUMENTS

| | | | | |
|---|---|---|---|---|
| CN | 1668697 | A | 9/2005 | |
| WO | WO-2011131642 | A1 * | 10/2011 | C08G 65/3344 |
| WO | 2017036533 | A1 | 3/2017 | |

OTHER PUBLICATIONS

Gjorevski et al., "Synthesis and characterization of well-defined hydrogel matrices and their application to intestinal stem cell and organoid culture", Nature Protocols, vol. 12, No. 11, Oct. 5, 2017 (Oct. 5, 2017), p. 2263-2274.

Gjorevski et al., "Designer matrices for intestinal stem cell and organoid culture", Nature, vol. 539, No. 7630, Nov. 16, 2016 (Nov. 16, 2016), p. 560-564.

Fisher et al., "Designing Peptide and Protein Modified Hydrogels: Selecting the Optimal Conjugation Strategy", Journal Of The American Chemical Society, vol. 139, No. 22, May 23, 2017 (May 23, 2017), p. 7416-7427.

Phelps et al., "Maleimide Cross-Linked Bioactive PEG Hydrogel Exhibits Improved Reaction Kinetics and Cross-Linking for Cell Encapsulation and In Situ Delivery", Advanced Materials, vol. 24, No. 1, Dec. 16, 2011 (Dec. 16, 2011), p. 64-70.

* cited by examiner

*Primary Examiner* — Evelyn Y Pyla
(74) *Attorney, Agent, or Firm* — COZEN O'CONNOR

(57) ABSTRACT

The present invention is related to a biofunctional three-dimensional hydrogel suitable for the expansion of freshly isolated or frozen intestinal cells and the formation of intestinal organoids therefrom, that avoids the use of a naturally-derived matrix such as Matrigel and provides intestinal organoids suitable for clinical applications and generated in a commercially feasible manner. The present invention is also related to a kit of parts comprising said hydrogel in combination with a suitable culture medium, and to a method of making organoids and expanding cells from freshly isolated or frozen intestinal cells with said kit of parts.

15 Claims, 2 Drawing Sheets

Specification includes a Sequence Listing.

METHOD FOR OBTAINING HEALTHY INTESTINAL ORGANOIDS

This application is a national stage application of PCT/EP2020/073586 filed on Aug. 24, 2020, which claims priority to European App. No. 19195855.2, filed on Sep. 6, 2019, the entirety of which is incorporated herein by reference.

SEQUENCE LISTING

The instant application contains a Sequence Listing which is submitted via the USPTO patent electronic filing system in TXT format (ACSII text) and is hereby incorporated by reference in its entirety. Said TXT file, created on May 13, 2025, is named 01001-GWLG (540725) ST25 substitute sequence listing and is 1,617 bytes in size.

The present invention is related to the field of regenerative medicine and precision medicine, and in particular to a method of preparing patient-derived healthy intestinal organoids (PDO).

The number of people affected by inflammatory bowel disease (IBD) continues to increase globally. Mucosal healing and re-establishment of intestinal barrier function are key treatment goals associated with substantially more favourable prognosis, lower relapse and hospitalization rates, as well as diminished risk of surgery and colorectal cancer. However, current medical treatments are not efficient in all IBD patients, with approximately 16-47% of patients requiring surgery 10 years after diagnosis (Frolkis et al., Risk of surgery for inflammatory bowel diseases has decreased over time: a systematic review and meta-analysis of population-based studies; Gastroenterology 2013; 145: 996-1006). This clearly highlights the unmet need for novel therapies, in which stem cell-enriched intestinal organoids hold great promise as a source of regenerative material for transplantation and re-establishment of intestinal barrier function. Organoids, including cell spheroids or clusters, are three-dimensional structures of stem cells or organ-specific cell types that develop from stem cells and self-organize (or self-pattern) through cell sorting and spatially restricted lineage commitment in a manner similar to the situation in vivo. An organoid therefore represents the native physiology of the cells and has a cellular composition (including remaining stem cells and/or specialized cell types at different stages of differentiation) and anatomy that emulate the native situation. Stem cells can be isolated from tissue or organoid fragments. The cells from which an organoid is generated can differentiate to form an organ-like tissue exhibiting multiple cell types that self-organize to form a structure very similar to the organ in vivo (i.e. cell differentiation). Organoids are therefore excellent models for studying human organs and human organ development in a system very similar to development in vivo. Organoids are also used to grow and expand cells for clinical applications. Organoids grown from isolated intestinal crypts or stem cells may also be referred to in the field as "enteroids" or "colonoids".

Intestinal organoids have successfully been delivered to mice with experimental colitis, demonstrating that the cells adhere to and become an integrated part of the epithelium (Yui et al., Functional engraftment of colon epithelium expanded in vitro from a single adult Lgr5+ stem cell, Nature medicine Vol. 18, no. 4 2012, 618-624; Fordham et al., Transplantation of Expanded Fetal Intestinal Progenitors Contributes to Colon Regeneration after Injury, Cell Stem Cell 13, 734-744, Dec. 5, 2013; and Sugimoto et al., Reconstruction of the Human Colon Epithelium In Vivo, Cell Stem Cell 22, 1-6, Feb. 1, 2018 (https://doi.org/10.1016/j.stem.2017.11.012)). In these studies, successful intestinal organoid growth and transplantation relied on the use of an animal derived matrix (such as Matrigel) for PDO establishment and expansion.

A 3D culture system for intestinal organoid growth in Matrigel was described that maintains basic crypt-villus physiology with stem cell turnover (Sato et al., Single Lgr5 stem cells build crypt-villus structures in vitro without a mesenchymal niche, Nature, Vol 459, 14 May 2009, 262-266; Sato et al., Paneth cells constitute the niche for Lgr5 stem cells in intestinal crypts, Nature, Vol 469, 20 Jan. 2011, 415-419; Sato et al., Longterm Expansion of Epithelial Organoids From Human Colon, Adenoma, Adenocarcinoma, and Barrett's Epithelium, GASTROENTEROLOGY 2011; 141:1762-1772; WO 2009/022907 A2; WO 2010/090513 A2; WO 2012/168930 A2; WO 2013/093812 A2). In these works, the identification of the suitable components for the cell culture media, which is used to feed cells grown in Matrigel, was the main issue.

However, batch-to-batch variation and undefined composition of animal derived matrices such as Matrigel prohibit regulatory approval for their use in humans. As such, to translate intestinal organoid transplantation therapy to human patients, several aspects of intestinal organoid culture need to be modified for clinical use. These include the development of a support matrix and of culture media that are defined and approved for human use, scalable, and preferably xeno-free (i.e. free from components of animal origin).

In Broguiere et al., Growth of Epithelial Organoids in a Defined Hydrogel, Adv. Mater. 2018, 1801621, defined but not synthetic (i.e. not allo-nor xeno-free) fibrin hydrogels supplemented with laminin-111 were shown to support the growth of intestinal organoids. The natural presence of RGD domains in fibrin was shown to be essential for organoid growth.

Gjorevski (Gjorevski et al., Designer matrices for intestinal stem cell and organoid culture, Nature, Vol 539, 24 Nov. 2016, 560-56; Gjorevski et al., Synthesis and characterization of well-defined hydrogel matrices and their application to intestinal stem cell and organoid culture, Nature protocols, Vol. 12, no. 11, 2017, 2263-2274; WO 2017/036533 A1 and WO 2017/037295 A1) developed enzymatically (factor XIII) crosslinked 8-arm polyethylene glycol (PEG) hydrogels with functionalized RGD peptides and different degradation kinetics, including specific enzymatic degradations as well as controlled self-degradation kinetics (hydrolysis of PEG-acrylate) for the growth of primary mouse and human small intestinal organoids and human colorectal cancer organoids. The addition of laminin-111 purified from mouse tissue (full protein) was necessary to support organoid differentiation.

While some success of this approach was shown for the expansion and organoid formation from mouse cells, it was not shown (and rather questioned in Gjorevski 2017, p. 2265) that the above systems were suitable for the expansion and organoid formation from freshly isolated or frozen human cells from a biopsy of a human. Also, the only tested system, that is based on an enzymatic crosslinking reaction with factor XIII, is expensive, difficult to up-scale and/or to automatize for commercial purposes, and has also proven to be difficult to reproduce.

The work described by Cruz-Acuna (Cruz-Acuna et al., Synthetic hydrogels for human intestinal organoid generation and colonic wound repair, Nature cell biology, advanced online publication published online 23 Oct. 2017; DOI: 10.1038/ncb3632, 1-23; Cruz-Acuna et al., PEG-4MAL hydrogels for human organoid generation, culture, and in vivo delivery, Nature protocols, Vol. 13, September 2018, 2102-2119; and WO 2018/165565 A1) is based on developing a completely synthetic 4-arm PEG-maleimide hydrogel functionalized with RGD and crosslinked with the protease-degradable peptide GPQ-W for the growth of intestinal organoids using human embryonic stem cells and induced pluripotent stem cells. Organoids expanded in these synthetic gels were then injected into a mouse colonic injury model as a proof-of-concept study demonstrating the therapeutic potential of intestinal organoid transplantation.

It has not been shown that with this system freshly isolated or frozen cells from a biopsy of a patient could be expanded and formed into organoids. For this system, it is necessary that the crosslinker component is enzymatically degradable.

Currently, the standard for the establishment of organoid cultures ex vivo includes firstly to encapsulate freshly isolated cells (from tissues) in the "gold standard" Matrigel (Matrigel® being one of the commercially available products of basement membrane extracts (BME)) and to grow the cells for several passages to expand them (i.e. to increase the cell number). BME (e.g. Matrigel) is a gel derived from mouse sarcoma extract, which as already noted above has poor batch-to-batch consistency, has undefined composition and therefore cannot be used for clinical translational applications, so that obtaining regulatory approval may be challanging or impossible (Madl et al., Nature 557 (2018), 335-342).

Removing the use of gels with undefined xeno components or human components for the establishment of organoids would overcome one of the main hurdles to use organoids in clinical applications, such as regenerative medicine, precision medicine, drug testing, or patient stratifications.

Proof of concept of freshly isolated cells from biopsies cultured in fully defined (not fully synthetic) matrices has been provided by Mazzocchi et al., In vitro patient-derived 3D mesothelioma tumor organoids facilitate patient-centric therapeutic screening, Scientific reports (2018) 8:2886; Votanopoulos et al., Appendiceal Cancer Patient-Specific Tumor Organoid Model for Predicting Chemotherapy Efficacy Prior to Initiation of Treatment: A Feasibility Study, Ann Surg Oncol (2019) 26:139-147; and WO 2018/027023 A1. Briefly, cells derived from mesothelioma and appendiceal cancer patients were cultured in hyaluronic acid/collagen-based hydrogels to develop a platform for drug response prediction. However, like Matrigel also Collagen is a naturally-derived matrix and suffers from similar problems.

So far, there has not been a report of a successful expansion of freshly isolated or frozen human cells from biopsies or tissue resections (i.e. cells which have been obtained directly from a human and which have not been pre-cultured or pre-established in another system) and subsequent formation of organoids therefrom in a fully defined and/or a fully synthetic hydrogel matrix that is not a naturally-derived matrix such as Matrigel or collagen. Despite the clear need for such an approach, as stated in the above discussed prior art, until now the gold standard still is the use of Matrigel for at least the first step of expansion of the cells. This is proof for the difficulties involved in making a semi-synthetic or fully synthetic three-dimensional hydrogel system work.

It was the problem underlying the present invention to provide a method for expansion of freshly isolated or frozen human cells from biopsies and subsequent formation of intestinal organoids therefrom, wherein said method completely avoids the use of a naturally-derived matrix such as Matrigel and provides intestinal organoids suitable for clinical applications and generated in a commercially feasible manner, i.e. cost-effective, reliable, reproducible, automatizable and up-scalable.

According to the present invention, said problem is solved by a hydrogel, a kit of parts and a method as defined in the independent claims.

In particular, the present invention is related to a biofunctional three-dimensional hydrogel suitable for the growth and expansion of freshly isolated or frozen intestinal cells and the formation of intestinal organoids therefrom, wherein said hydrogel is the reaction product of at least one precursor molecule, which is a multi-arm PEG containing ethylenically unsaturated groups selected from the group consisting of vinylsulfone and acrylate moieties, a crosslinker molecule containing at least two, preferably two nucleophilic groups capable of reacting with said ethylenically unsaturated groups of said multi-arm PEG in a Michael addition reaction, and at least one biofunctional ligand selected from the group consisting of natural laminins, for example laminin-111, recombinant laminin isoforms, preferably laminin-511, and biofunctional fragments thereof, characterized in that the crosslinker molecule comprises at least one RGD motif and preferably it is not known to be enzymatically degradable.

Compared to the prior-art hydrogels from Gjorevski 2016 & 2017, WO 2017/036533 A1 and WO 2017/037295 A1, the hydrogel of the present invention is less expensive. Since it does not require the presence of enzymes and activating factors for crosslinking, the hydrogel of the present invention can be easily upscaled for commercial purposes. And this is also because gel precursors described above in this invention (i.e. multi-arm PEG containing ethylenically unsaturated groups, crosslinker molecule containing two nucleophilic groups, and the at least one biofunctional ligand) do not require additional steps for the preparation of the gel precursor as it is required in the prior art gels from Gjorevski 2016 & 2017, WO 2017/036533 A1 and WO 2017/037295 A1. Especially, it is very suitable for manufacturing upscale and automatization of their use, i.e. for the application of the method using pipetting robots etc. The hydrogel of the present invention is very reliably reproducible. Furthermore, in contrast to the enzymatically crosslinked gel of Gjorevski et al., the hydrogel of the present invention is compatible with commercially available culture media, e.g. IntestiCult™ Organoid Growth Medium from STEMCELL Technologies, i.e. it does not disintegrate prematurely.

As compared to the prior-art hydrogels from Cruz-Acuna 2017 & 2018 and WO 2018/165565 A1, the hydrogel of the present invention is based on a different chemistry, more suitable for automatization, i.e. for the application of the method using pipetting robots etc., and can be up-scaled more easily. This is because, during the manufacturing process all gel precursor materials of the present invention (i.e. multi-arm PEG containing ethylenically unsaturated groups, crosslinker molecule containing two nucleophilic groups, and the at least one biofunctional ligand) can be premixed and lyophilized without reacting prematurely, which is not possible with the system described by Cruz-Acuna et al., as their precursors would react under those conditions.

An important aspect of the hydrogel of the present invention is the fact that the at least one RGD motif is provided within the crosslinker molecule, as compared to the prior art hydrogels where the RGD motif is provided in a ligand that is attached (in a "dangling" manner) to the crosslinked hydrogel. The approach of the present invention allows the increase of the amount of RGD motifs in the hydrogel to a considerable extent. It has been surprisingly found that this results in a significant improvement of the hydrogel characteristics for the purposes of the present invention.

According to the present invention, it has been surprisingly found that the hydrogels discussed herein are suitable for de novo formation of organoids from freshly isolated or frozen intestinal cells (single cells and/or clusters) from a human biopsy or tissue resection, the growth, passaging and expansion of these cells and optionally subsequent differentiation of organoids therefrom, when used in combination with a suitable culture medium. Thus, according to the present invention, the necessity of having to use a naturally-derived matrix such as Matrigel is completely avoided.

According to the present invention, the term "freshly isolated or frozen human cells from biopsies or tissue resections" refers to cells which have been obtained directly from a human by any of the mentioned procedures and which have not been pre-cultured or pre-established in another system before being used in a method of forming organoids. Typically, such fresh cells are collected and used in the method of the present invention immediately or within a period of up to 3 to 4 days. If the cells are not used immediately after collection, they may be frozen for storage purposes, under conventionally used conditions. The collected cells may be single and/or "clusters" of cells, including dissociated cells, crypts and pieces of tissue. According to a preferred embodiment of the present invention, epithelial cells are used.

According to the present invention, the term "de novo formation of organoids" refers to freshly isolated or frozen human cells (e.g. human biopsy or tissue resection) that have been grown ex-vivo (i.e. outside the original organism) for the first time. The terms "First ex-vivo cell growth" or "Passage zero (PO)" can be used synonymously.

According to the present invention, the term "Pre-established organoids" refers to cells, single cells and/or cell clusters (e.g. cell aggregates, organoids, etc.) that have been grown in other systems (e.g. Matrigel, 2D or 3D systems, in vivo as patient-derived xenografts (PDX)) before being applied to the hydrogel of the present invention.

According to the present invention, the term "cell growth" refers to the successful growth of cells from pre-established organoids or de novo formed organoids.

According to the present invention, the term "Cell passaging" or "passage" or "cell splitting" refers to the steps of extracting cells from one gel and seeding and growing those cells in another gel having the same or different characteristics as/than the previous gel.

According to the present invention, the term "Cell expansion" refers to the steps of cell growth and cell number increase (e.g. within the same passage or from one passage to the next one).

According to the present invention, the term "Organoid differentiation" refers to the successful induction of cell differentiation in an organoid.

The present invention is also related to a kit of parts for the growth and expansion of freshly isolated or frozen intestinal cells and the formation of intestinal organoids therefrom, comprising at least one precursor molecule, which is a multi-arm PEG containing ethylenically unsaturated groups selected from the group consisting of vinylsulfone and acrylate moieties, a crosslinker molecule containing at least two, preferably two nucleophilic groups capable of reacting with said ethylenically unsaturated groups of said multi-arm PEG in a Michael addition reaction, wherein the crosslinker molecule comprises at least one RGD motif, and at least one biofunctional ligand selected from the group consisting of natural laminins, for example laminin-111, recombinant laminin isoforms, preferably laminin-511, and biofunctional fragments thereof, and a culture medium, wherein said culture medium comprises R-spondin 1, preferably R-spondin 1 conditioned medium, and Wnt3a, preferably Wnt3a conditioned medium.

The present invention is also related to a method for the growth and expansion of freshly isolated or frozen intestinal cells, comprising the steps:

a) de novo formation of organoids from freshly isolated or frozen human intestinal cells, using a kit of parts as described herein, by incubating the hydrogel of said kit with said freshly isolated or frozen intestinal cells in the presence of the culture medium of said kit, b) growing, optionally passaging, and expanding of cells from the intestinal organoids from step a) using said kit of parts as described herein, c) optionally differentiation of the organoids from step a), in the presence of a modified culture medium inducing cell differentiation, characterized that in said method only fully synthetic or fully defined semi-synthetic hydrogels are used.

According to the present invention the term "fully synthetic hydrogel" refers to a hydrogel that has been formed exclusively from synthetic precursors, i.e. in the absence of any naturally derived precursor such as natural laminin-111.

According to the present invention the term "fully defined semi-synthetic hydrogel" refers to a hydrogel that comprises at least one naturally derived precursor such as natural laminin-111, but has a fully defined structure and/or composition, due to the known nature of the precursor molecules used for its synthesis. A fully defined semi-synthetic hydrogel thus differs from naturally-derived hydrogels such as Matrigel, which have an unknown structure and/or composition.

The hydrogel of the present invention is based on a multi-arm PEG (poly(ethylene glycol)) containing ethylenically unsaturated groups selected from the group consisting of vinylsulfone or acrylate moieties, as a precursor molecule.

A hydrogel (gel) is a matrix comprising a network of hydrophilic polymer chains. A biofunctional hydrogel is a hydrogel that contains bio-adhesive (or bioactive) molecules, and/or cell signalling molecules that interact with living cells to promote cell viability and a desired cellular phenotype.

According to a preferred embodiment of the present invention, the multi-arm PEG is selected from the group consisting of PEG bearing 2 to 12 arms, preferably 4-arms or 8-arms, i.e. preferably is a 4-arm or 8-arm PEG. The PEG can have a molecular weight from 1,000-1,000,000, from 1,000-500,000, from 1,000-250,000, from 1,000-150,000, from 1,000-100,000, from 1,000-50,000, from 5,000-100,000, from 5,000-50,000, from 10,000-100,000, from 10,000-50,000, from 20,000-100,000, from 20,000-80,000, from 20,000-60,000, from 20,000-40,000, or from 40,000-60,000. The above molecular weights are average molecular weights in Da., as determined by e.g. methods such as GPC or MALDI.

Such PEGs are known in the art and commercially available. They consist of a core that in case of a 4-arm PEG may be pentaerythritol, and in the case of an 8-arm PEG may be tripentaerythritol or hexaglycerol:

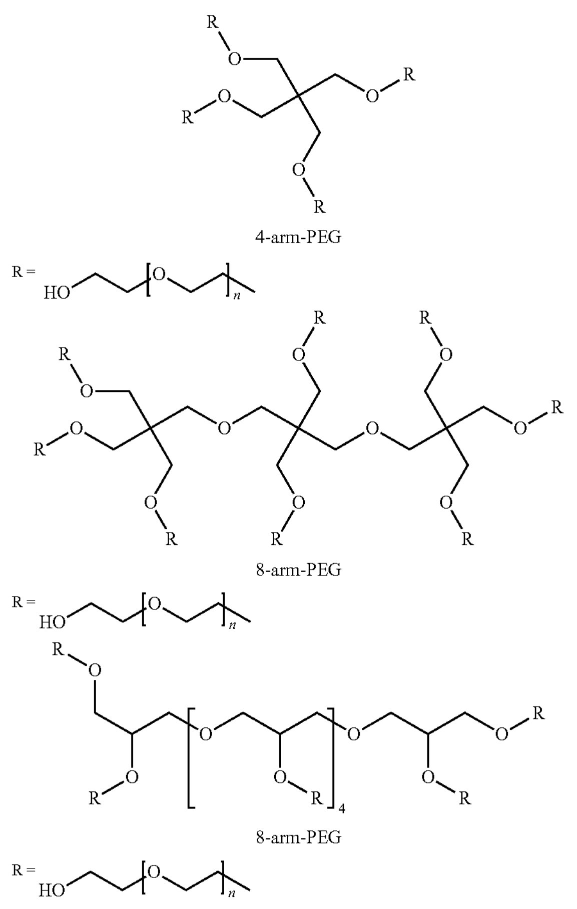

4-arm-PEG 8-arm-PEG 8-arm-PEG

In a 4-arm PEG-VS or 8-arm PEG-VS, the terminal free OH groups of the above 4-arm PEG or 8-arm PEG are converted under conditions known in the art into vinylsulfone groups, so that in the above formulas R becomes for example

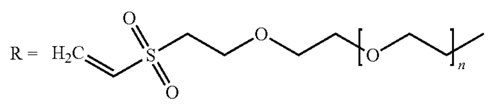

In a 4-arm PEG-Acr or 8-arm PEG-Acr, the terminal free OH groups of the above 4-arm PEG or 8-arm PEG are converted under conditions known in the art into acrylate groups, so that in the above formulas R becomes for example

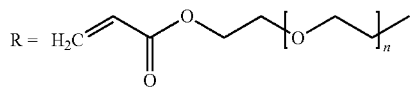

Preferably, all terminal free OH groups of the above 4-arm PEG or 8-arm PEG are converted into vinylsulfone or acrylate moieties.

Vinylsulfone or acrylate moieties are ethylenically unsaturated groups that are suitable for crosslinking the PEG precursor molecules via a Michael addition reaction. The Michael addition reaction is a well-known chemical reaction that involves the reaction of a suitable nucleophilic moiety with a suitable electrophilic moiety. It is known that, for example, acrylate or vinylsulfone moieties are suitable Michael acceptors (i.e. electrophiles) that react with e.g. thiol moieties as suitable Michael donors (i.e. nucleophiles).

For obtaining the hydrogel according to the present invention, the above PEG precursor molecule is accordingly reacted with a crosslinker molecule containing at least two, preferably two nucleophilic groups capable of reacting with said ethylenically unsaturated groups of said multi-arm PEG in a Michael addition reaction.

A crosslinker molecule is a molecule that connects at least two of the above PEG precursor molecules with each other. For that purpose, the crosslinker molecule has to possess at least two, preferably two of the above nucleophilic groups, so that one nucleophilic group reacts with the first PEG precursor molecule and the other nucleophilic group reacts with a second PEG precursor molecule.

While it would be principally possible that the crosslinker molecule to be used in the present invention comprises more than two of the above nucleophilic groups, this is not necessary for the formation of a three-dimensional network, since each of the PEG precursor molecules may react with more than one of said crosslinker molecules.

An important aspect of the hydrogel of the present invention is the fact that the at least one RGD motif is provided within the crosslinker molecule, as compared to the prior art hydrogels where the RGD motif is provided in a ligand that is attached (in a "dangling" manner) to the crosslinked hydrogel. The approach of the present invention allows the increase of the amount of RGD motifs in the hydrogel to a considerable extent. It has been surprisingly found that this results in a significant improvement of the hydrogel characteristics for the purposes of the present invention.

For the hydrogel of the present invention, the presence of a considerable amount of RGD motifs in the hydrogel is necessary. The result described in WO 2017/037295 A1 that RGD motifs would be dispensable if laminin-111 ligands were provided in the hydrogel, could not be confirmed for the hydrogel of the present invention.

Accordingly, the crosslinker molecule to be used in the present invention is a peptide comprising at least one RGD motif, preferably at least two RGD motifs, more preferably 2 to 8 RGD motifs, even more preferably 2 to 5 RGD motifs, and especially preferred 2, 3 or 4 RGD motifs.

The term RGD or RGD sequence refers to a minimal bioactive RGD sequence, which is the Arginine-Glycine-Aspartic Acid (RGD) sequence, and which is the smallest (minimal) fibronectin-derived amino acid sequence that is sufficient to mimic cell binding to fibronectin and/or to promote adhesion of the anchorage-dependent cells. Moreover, lysine- or arginine-containing amino acid sequences, such as RGD, are suitable substrates for proteases such as trypsin-like enzymes used e.g. for gel dissociation.

Examples of suitable RGD motifs are RGD, RGDS (SEQ ID NO. 1), RGDSP (SEQ ID NO. 2), RGDSPG (SEQ ID NO. 3), RGDSPK (SEQ ID NO. 4), RGDTP (SEQ ID NO. 5) or RGDSPASSKP (SEQ ID NO. 6), but principally any known and successfully employed RGD sequences, in the field of hydrogels and cell culture, could be used.

According to a preferred embodiment of the present invention, said crosslinker molecule is a peptide comprising at least two RGD motifs and at least two cysteine moieties. Cysteine is an amino acid that comprises a thiol group, i.e. a Michael donor moiety.

According to an especially preferred embodiment of the present invention, said crosslinker molecule is Ac-GCRE-GRGDSPGGRGDSPGERCG-$NH_2$ (SEQ ID NO. 7).

According to the present invention, the amount of RGD motifs in the hydrogel is larger than in the prior art hydrogels discussed above (in WO 2017/037295 A1, p. 31, example 5 it was discussed that raising the amount of RGD in the hydrogel above 0.5 mM would not lead to any improvement; in the Cruz-Acuna gels (Cruz-Acuna 2017) an amount of 2 mM RGD was consistently used). According to the present invention, the amount of RGD motifs in the hydrogel is in the range of 1 to 15 mM, preferably 2.5 to 5.5 mM and especially preferred 2.5 to 5 mM.

Crosslinking of the hydrogel precursor molecules is usually done in the presence of cell types to be cultured within the hydrogel, in such a way that the single cells and/or "clusters" of cells, including dissociated cells, crypts and pieces of tissue, are encapsulated by the forming hydrogel matrix, i.e. are residing in a distinct cell culture microenvironment.

According to an especially preferred embodiment of the present invention, said hydrogel is

- either the reaction product of a 4-arm or 8-arm PEG vinylsulfone crosslinked with a peptide comprising at least two, preferably two, thiol groups and at least two, preferably two RGD motifs, or
- comprises the reaction product of a 4-arm or 8-arm PEG vinylsulfone crosslinked with a peptide comprising at least two, preferably two, thiol groups and at least two, preferably two RGD motifs, and/or the reaction product of a 4-arm or 8-arm PEG acrylate crosslinked with a peptide comprising at least two, preferably two, thiol groups and at least two, preferably two RGD motifs.

In each embodiment, additionally a biofunctional ligand selected from the group consisting of natural laminins, for example laminin-111, recombinant laminin isoforms, and biofunctional fragments thereof is present in the hydrogel. Examples of suitable recombinant laminin isoforms are laminin-111, laminin-211, laminin-332, laminin-411, laminin-511, or laminin-521, laminin-511 being preferred.

The first of these embodiments thus uses as a precursor molecule only a 4-arm or 8-arm PEG vinylsulfone. The hydrogel according to said embodiment is mechanically stable, i.e. it does not undergo any decrease of its shear modulus and thus does not soften over time.

The second of these embodiments thus uses as precursor molecules both a 4-arm or 8-arm PEG vinylsulfone and a 4-arm or 8-arm PEG acrylate, or alternatively solely a 4-arm or 8-arm PEG acrylate. As will be discussed below, the presence of a 4-arm or 8-arm PEG acrylate in the hydrogel renders the hydrogel mechanically dynamic, i.e. it undergoes a decrease of its shear modulus and thus softens over time. The degree of softening of the hydrogel can be adjusted by the ratio in which 4-arm or 8-arm PEG vinylsulfone and 4-arm or 8-arm PEG acrylate are present in the hydrogel. According to an especially preferred embodiment of the present invention, the ratio in which 4-arm or 8-arm PEG vinyl-sulfone and 4-arm or 8-arm PEG acrylate are present in the hydrogel is 5:1 to 1:5, preferably 3:1 to 1:3, especially preferred 1:1.

It has been found that the embodiment with the mechanically dynamic hydrogel, preferably with a ratio in which 4-arm or 8-arm PEG vinylsulfone and 4-arm or 8-arm PEG acrylate are present in the hydrogel of 1:1, is preferred with respect to its suitability for expansion and passaging (more efficient gel dissociation and reduced cell loss as compared to a non-degradable gel with otherwise similar structure) of the freshly isolated or frozen intestinal cells. Moreover, it has been surprisingly found that the hydrogels of the present invention show a highly advantageous dynamic degradation behaviour. In contrast to hydrogels from the prior art (from Gjorevski 2016 & 2017, WO 2017/036533 A1 and WO 2017/037295 A1), which degrade prematurely under the culturing conditions suitable for the present invention (i.e. in the presence of the most preferred culture media of the present invention) and thus are not suitable for cell passaging and expansion, the hydrogels of the present invention have been found to be still present (i.e. not degraded) after the usually required period of 8-11 days and especially are then in a condition that is optimal for cell passaging and further cell expansion.

The hydrogel according to the present invention furthermore comprises as an essential component at least one biofunctional ligand selected from the group consisting of natural laminins, for example laminin-111, recombinant laminin isoforms, and biofunctional fragments thereof. Examples of suitable recombinant laminin isoforms are laminin-111, laminin-211, laminin-332, laminin-411, laminin-511, or laminin-521.

Preferably, at least one biofunctional ligand selected from the group consisting of natural laminins, for example laminin-111, recombinant laminin isoforms, and biofunctional fragments thereof is present in the hydrogel at a concentration of 0.01 g/l-3 g/l, more preferably 0.05 g/l-0.5 g/l.

Laminins are a family of extracellular matrix glycoproteins that have a heterotrimeric structure consisting of an $\alpha$, $\beta$ and $\gamma$ chain. For example, the "111" identifies the isoform's chain composition of $\alpha1\beta1\gamma1$. Laminin-111 is synonymous with Laminin-1. In cell adhesion laminin-111 and other isoforms are important proteins that anchor cells to the extracellular matrix (ECM). The linkage between cells and the ECM is formed by binding cell surface receptors to one end of the laminin a chain and binding ECM components to another region of the laminin. Globular domains (G-Domain) of the a chain are the regions on laminin-111 that allow the binding of integrins, glycoproteins, sulfated glycolipids and dystroglycan. Besides anchoring cells to the ECM, laminins are also involved in the signalling of cells and other components of the ECM.

According to one embodiment, a natural laminin, for example laminin-111, preferably a mouse laminin-111, is used. In said case, the hydrogel of the present invention is semi-synthetic, since the natural laminin-111 is of biological origin. However, since the structure of natural laminin-111, preferably a mouse laminin-111, is known, the hydrogel of the present invention is fully defined and thus reliably reproducible.

According to another embodiment, a recombinant laminin isoform is used. Examples of suitable recombinant laminin isoforms are laminin-111, laminin-211, laminin-332, laminin-411, laminin-511, or laminin-521, preferably laminin-511. In said case, the hydrogel of the present invention is fully synthetic, since also the laminin isoform is of synthetic origin. Methods of making recombinant laminin isoforms are known in the art and do not need to be discussed here.

According to another embodiment, a biofunctional fragment of laminin-511 is used. A biofunctional fragment of laminin-511 is a molecule that comprises a portion of the full laminin-511 that provides the necessary biological function. In other words, said fragment has to include one of the portions of the full laminin-511 that can interact with other molecular components (e.g. integrins, cell surface receptor proteins, components of the ECM).

The embodiments avoiding the use of natural laminin-111 are preferred, since they provide a fully synthetic three-dimensional matrix and thus advantages with respect to regulatory approval for their use in clinical applications.

According to another embodiment, in addition to a biofunctional ligand selected from the group consisting of natural laminin-111, recombinant laminin isoforms, and biofunctional fragments thereof, the hydrogel of the present invention may furthermore comprise at least one other biofunctional ligand. For example, a ligand comprising at least one RGD motif as discussed above may be attached to the hydrogel.

The at least one biofunctional ligand may be attached to the crosslinked hydrogel by methods known in the art, here preferably by reaction of a thiol group of a cysteine in the biofunctional ligand with a Michael acceptor group (vinylsulfone or acrylate) in the hydrogel polymer.

Another aspect of the invention relates to a method of preparing three-dimensional hydrogels of the invention. In particular, this method comprises the steps of a1) dispensing one or more different hydrogel precursor molecules, which is a multi-arm PEG containing ethylenically unsaturated groups selected from the group consisting of vinylsulfone and acrylate moieties, onto a substrate or into discrete volumes of a substrate, preferably a multi-well plate, and adding to said hydrogel precursor molecules
 one or more crosslinker molecules containing at least two, preferably two nucleophilic groups capable of reacting with said ethylenically unsaturated groups of said multi-arm PEG in a Michael addition reaction, wherein said crosslinker molecule comprises at least one RGD motif, and
 at least one biofunctional ligand selected from the group consisting of natural laminins, for example laminin-111, recombinant laminin isoforms, preferably laminin-511, and biofunctional fragments thereof; or a2) dispensing a resuspended unreacted powder, preferably a lyophilized unreacted powder, onto a substrate or into discrete volumes of a substrate, preferably a multi-well plate, wherein said unreacted powder comprises
 one or more different hydrogel precursor molecules, which is a multi-arm PEG containing ethylenically unsaturated groups selected from the group consisting of vinylsulfone and acrylate moieties
 one or more crosslinker molecules containing at least two, preferably two nucleophilic groups capable of reacting with said ethylenically unsaturated groups of said multi-arm PEG in a Michael addition reaction, wherein said crosslinker molecule comprises at least one RGD motif, and
 at least one biofunctional ligand selected from the group consisting of natural laminins, for example laminin-111, recombinant laminin isoforms, preferably laminin-511, and biofunctional fragments thereof b) adding cells, preferably freshly isolated or frozen intestinal cells from a biopsy of a human, onto the substrate or into said discrete volumes of the substrate or into the hydrogel precursor formulations of a1) or a2) before addition onto the substrate or into said discrete volumes of the substrate; and c) crosslinking said hydrogel precursor molecules and said crosslinker molecules to form a hydrogel.

According to a preferred embodiment, a hydrogel precursor formulation in the form of an unreacted powder is resuspended and dispensed onto or into discrete volumes of a substrate, preferably a multi-well plate. Said hydrogel precursor formulation comprises all the components required for the formation of a hydrogel according to the present invention, i.e. the above discussed one or more different hydrogel precursor molecules, one or more crosslinker molecules, and the at least one biofunctional ligand, and preferably also the cells, preferably freshly isolated or frozen intestinal cells from a biopsy of a human.

The provision of said unreacted powder of said hydrogel precursor formulation is known in the art, e.g. from WO 2011/131642 A1.

According to another embodiment, also the hydrogel precursor formulation as such, i.e. without prior lyophilization and resuspension, can be dispensed onto or into discrete volumes of the substrate.

The hydrogel of the present invention is a so-called soft hydrogel, i.e. the three-dimensional hydrogel of the invention typically has a shear modulus (stiffness) of 50 to 1000 Pa, preferably 200 to 500 Pa. The desired stiffness range is achieved by fixing the sum of the polymer (PEG) content and the crosslinker content within the hydrogel accordingly, preferably to 1.0-10% w/v.

In one embodiment of the present invention, the hydrogel is self-degradable. This is achieved by the presence of acrylate moieties in the hydrogel precursor molecules, since those moieties undergo hydrolysis (i.e. their bonds are broken in the presence of water), as known in the art (Gjorevski 2016, p. 563, FIG. 4*a*). Accordingly, in said embodiment, the three-dimensional hydrogels of the invention have an initial shear modulus (stiffness) of 50 to 1000 Pa, preferably 200 to 500 Pa, and a final shear modulus (stiffness) of 0-50 Pa, preferably 0 Pa. Said final shear modulus (stiffness) is typically reached 7-18 days after formation of the hydrogel.

The shear modulus of a hydrogel is equivalent to the modulus of rigidity, G, elastic modulus or elasticity of a hydrogel. The shear modulus is defined as the ratio of shear stress to the shear strain. The shear modulus of a hydrogel can be measured using a rheometer. In brief, preformed hydrogel discs 1-1.4 mm in thickness are allowed to swell in complete cell culture medium for at least 3 h, and are subsequently sandwiched between the parallel plates of the rheometer. The mechanical response of the gels is recorded by performing frequency sweep (0.1-10 Hz) measurements in a constant strain (0.05) mode, at room temperature. The shear modulus (G') is reported as a measure of gel mechanical properties.

The technical properties of 3D hydrogels can be adjusted by varying the hydrophilic polymer content in the hydrogel, as well as the molecular weight and/or functionality (number of sites available for crosslinking) of the polymeric hydrogel precursors.

The sum of the polymer (i.e. the PEG molecules) content and the crosslinker content of the hydrogels, swollen to equilibrium in a buffer, can range between 0.3 and 10% w/v, with preferred ranges of 1.1 to 4.0% % w/v and 1.5 to 3.5% w/v.

Unlike the teaching of Cruz-Acuna 2017 & 2018 and WO 2018/165565 A1, according to the present invention it was found that the provision of enzymatically degradable sites in the hydrogel is not preferred with respect to the efficacy of the hydrogel for the purposes of the present invention. Therefore, the hydrogels of the present invention preferably are insensitive to enzymatic degradation that requires specific enzymatically cleavable peptide sequences, such as MMP or cathepsin degradation, i.e. they do not contain any moiety that is susceptible to enzymatic cleavage by cell-secreted proteases.

The microenvironment provided by the hydrogel of the present invention provides the biochemical, biophysical and biological complexity required for organoid formation from freshly isolated or frozen cells or tissue of a human.

According to the present invention, it has been found that the hydrogels described herein are suitable for the expansion of freshly isolated or frozen intestinal cells and the formation of intestinal organoids therefrom, when used in combination with an appropriate culture medium.

It has been found that in order to expand freshly isolated or frozen intestinal cells and to form intestinal organoids therefrom, a culture medium has to be used that comprises as essential components Wnt agonists such as R-spondin1, preferably R-spondin1 conditioned medium, and Wnt3a, preferably Wnt3a conditioned medium.

R-spondin1 can be used in the form of a conditioned medium, e.g. the supernatant of cells that were stably transfected to secrete R-spondin1. Alternatively, recombinant R-spondin1, preferably purified recombinant R-spondin1, can be used.

Wnt3a is preferably used in the form of a conditioned medium, e.g. the supernatant of cells that were stably transfected to secrete Wnt3a. However, it has been shown that afamin stabilizes Wnt proteins (Mihara et al. Active and water-soluble form of lipidated Wnt protein is maintained by a serum glycoprotein afamin/a-albumin eLife 2016; 5: e11621). The complex afamin/recombinant Wnt3a or other similar complexes allowing the stabilization of Wnt protein can also be used instead of the conditioned medium (Holmberg et al., Culturing human intestinal stem cells for regenerative applications in the treatment of inflammatory bowel disease. EMBO Mol Med 2017 9:558-57). Also a Wnt surrogate protein as described in Janda, Surrogate Wnt agonists that phenocopy canonical Wnt/β-catenin signaling, Nature 2017 May 11; 545 (7653): 234-237; and WO 2016/040895 A1, can be used.

According to a preferred embodiment of the present invention, said culture medium additionally comprises FBS (fetal bovine serum).

Optionally, one or more of the following components may be present in the culture medium: basal medium components such as adDMEM/F12, amino acids such as glutamine, proteins such as transferrin, noggin, for example recombinant murine noggin, and epidermal growth factor (EGF), for example recombinant murine EGF, antibiotics such as Penicillin-Streptomycin, antioxidants such as Glutathione, N-acetyl-l-cysteine (NAC), Catalase, and Superoxide Dismutase, vitamins such as Biotin, L-Carnitine, Vitamin E, Vitamin A, Nicotinamide, hormones such as Triiodo-L-thyronine (T3), Corticosterone, Progesterone and Insulin, fatty acids such as Linoleic acid or Linolenic acid, sugars such as D-Galactose, inhibitors such as A83-01 (ALK inhibitor), SB202190 (p38 inhibitor), or Y-27632 (ROCK inhibitor), and additional component such as Putrescine, Ethanolamine HCl, HEPES or Sodium selenite.

In table 1 below a preferred embodiment of culture media (Standard culture medium (SCM) and Differentiation medium (DM) composition) suitable for the present invention is described:

TABLE 1

| Reagent information | | Media composition | |
|---|---|---|---|
| Reagent | Concentration | SCM | DM |
| Advanced DMEM/F12 | — | x | x |
| GlutaMAX supplement (100×) | 1× | x | x |
| HEPES | 1 to 10 mmol/L | x | x |
| Pen-Strep (100×) | 1× | x | x |
| Wnt3a conditioned medium | 50 % of the total volume | x | — |
| R-Spol conditioned medium | 10 % of the total volume | x | — |
| B-27 supplement (50×) | 1× | x | x |
| N-2 supplement (100×) | 1× | x | x |
| Nicotinamide | 10 mmol/L | x | — |
| n-acetylcysteine | 1 to 1000 μmol/L | x | x |
| A83-01 | 0.5 μmol/L | x | x |
| Recombinant murine EGF | 50 ng/mL | x | x |
| Recombinant murine Noggin | 100 ng/mL | x | x |
| SB202190 | 10 μmol/L | x | — |

A commercially available culture medium which is suitable for the present invention is IntestiCult™ (available from STEMCELL Technologies).

According to the present invention, it has been found that the above described commercially available culture medium (IntestiCult™) may not be used with the hydrogels from the prior art, e.g. from Gjorevski 2016 & 2017, WO 2017/036533 A1 and WO 2017/037295 A1. The hydrogels from the prior art degrade prematurely within said culture media, within typically one day. The hydrogels of the prior art cannot be kept in these culture media for a period of time sufficient for cell growth and expansion.

The present invention is also related to a method for the growth and expansion of freshly isolated or frozen intestinal cells, comprising the steps:

a) de novo formation of organoids from freshly isolated or frozen human intestinal cells, using a kit of parts as described herein, by incubating the hydrogel of said kit with said freshly isolated or frozen intestinal cells in the presence of the culture medium of said kit,
b) growing, optionally passaging, and expanding of cells from the intestinal organoids from step a) using said kit of parts as described herein,
c) optionally differentiation of the organoids from step a), in the presence of a modified culture medium inducing cell differentiation, characterized that in said method only fully synthetic or fully defined semi-synthetic hydrogels are used.

Thus, the method of the present invention completely avoids the necessity of having to use a naturally-derived matrix such as Matrigel.

The cells to be used in the method of the present invention can be obtained by a suitable method, e.g. by a standard sigmoidoscopy where 1 to several, for example 5, standard punch biopsies are obtained.

The thus obtained cells may be isolated by standard procedures known in the art, e.g. by chelation (using a chelating agent such as EDTA) and made to single or "clusters" of cells, including dissociated cells, crypts and pieces of tissue, by standard procedures known in the art, e.g. by trypsin-like enzymes exposure.

The thus obtained single cells or "clusters" of cells, including dissociated cells, crypts and pieces of tissue, are subsequently expanded in vitro for a few passages (e.g. 2 passages) to obtain enough cells for the desired clinical application (e.g. minimum $10^7$ cells for regenerative medicine) using the kit of parts of the present invention, i.e. in the hydrogel of the present invention in combination with the culture medium defined above. During the cell expansion, the culture medium is hereby exchanged regularly, for example every 2 to 4 days.

The thus obtained organoids can be implanted into the patient by standard procedures known in the art, for example using a standard colonoscopy catheter.

Thus, in a further aspect, the invention provides a method for intestinal tissue regeneration comprising a) encapsulating and expanding of freshly isolated or frozen intestinal cells from a human biopsy in the three-dimensional hydrogel of the invention, and forming therein organoids, and b) transplanting the formed organoids or cells into the patient.

With the method of the present invention, it is possible to maintain freshly isolated or frozen intestinal cells for at least 10 passages with an organoid forming capacity comparable to that of Matrigel, as well as with similar numbers of expanded cells as in Matrigel. The present invention allows organoid production that complies with relevant regulatory requirements for use in humans and/or clinical applications.

EXAMPLES

The present invention will now be explained in more detail with reference to non-limiting drawings and embodiments.

Figure 1:
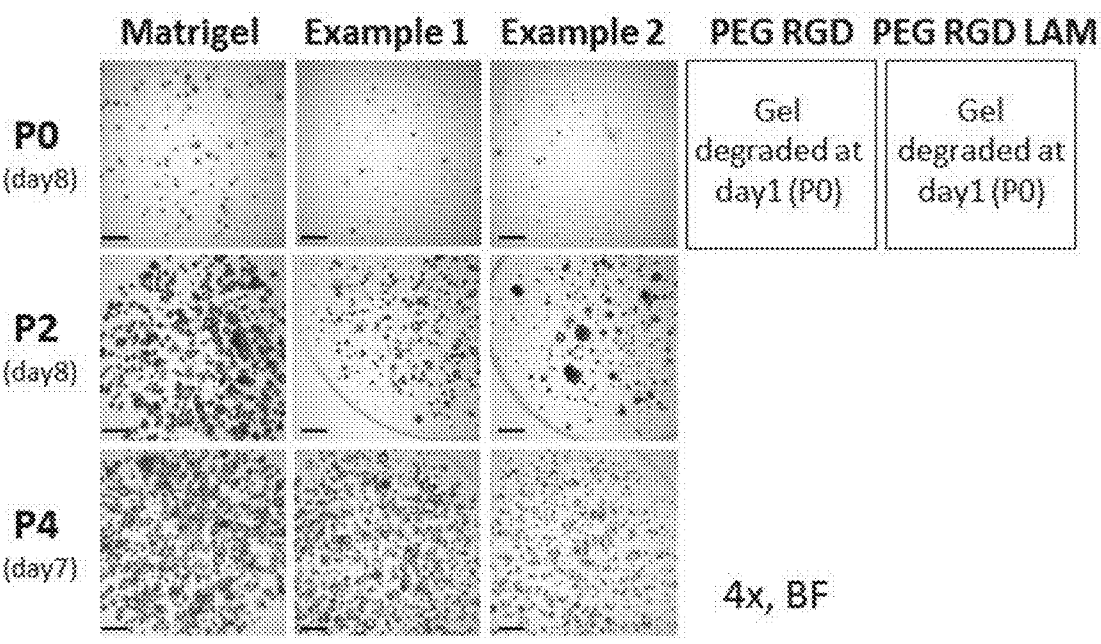
FIG. 1 shows the organoid formation from intestinal cells freshly isolated from human biopsy at different culture passages (P, day indicated in brackets), cultured in a hydrogel according to example 1 (fully defined semi-synthetic), hydrogels according to example 2 (synthetic), prior art gels (PEG RGD and PEG RGD LAM) or Matrigel using the commercial culture medium IntestiCult™. Scale bar=500 μm.

MATERIALS AND METHODS a) Isolation of Cells from Human Colonic Biopsies and First Encapsulation Colonic punch biopsies were attained from healthy control subjects after signed informed consent of patients. Intestinal cells were isolated by chelation (using EDTA) and made to single cells by enzymatic dissociation using TrypLE Express (Thermo Fisher Scientific). Single cells from freshly dissociated biopsy were resuspended in a suitable volume of basal medium (DMEM/F12, GlutaMAX (1×), Pen-Strep (100 U/ml) (Thermo Fisher Scientific) and HEPES (10 mM) (Thermo Fisher Scientific)) to obtain 2500 cells/μl (5× final concentration) and to be ready for the first encapsulation (passage 0) in Matrigel, fully defined semi-synthetic (Example 1) or synthetic (Example 2) hydrogels and prior art gels (PEG RGD and PEG RGD LAM).

The prior art hydrogels PEG RGD and PEG RGD LAM were prepared as described in Gjorevski et al., Synthesis and characterization of well-defined hydrogel matrices and their application to intestinal stem cell and organoid culture, Nature protocols, Vol. 12, no. 11, 2017, 2263-2274. Briefly, to create hydrogel precursors, 8-arm PEG-VS and 8-arm PEG-Acr macromers were end-functionalized with lysine- and glutamine-presenting peptides that serve as substrates for the activated transglutaminase factor XIII (FXIIIa). The crosslinking of the macromers and resulting gel formation occurred through the FXIIIa-mediated formation of ε-(α-glutamyl) lysine isopeptide side-chain bridges between the two peptide substrates. Using the same crosslinking mechanism RGD containing peptide sequences were conjugated to the hydrogel backbone. For PEG RGD LAM, additionally natural mouse laminin-111 was added to the hydrogel.

The hydrogel used in example 1 was derived from a 1:1 ratio of 8-arm PEG-VS and 8-arm PEG-Acr as precursor molecules, a peptidic crosslinker molecule comprising two cystein moeities and two RGD motifs and not being enzymatically degradable, and natural mouse laminin-111 as biofunctional molecule.

The hydrogel used in example 2 was derived from a 1:1 ratio of 8-arm PEG-VS and 8-arm PEG-Acr as precursor molecules, a peptidic crosslinker molecule comprising two cystein moeities and two RGD motifs and not being enzymatically degradable, and recombinant laminin-511 as biofunctional molecule.

Gel and cells (approximately 10000 cells) mixture was casted in 20 μl droplets in 48-well plates and placed at 37° C. The assay plate was inverted every other minutes until gelation occurs to avoid cell sedimentation. After 20 min, 300-330 μl of IntestiCult™ medium supplemented with ROCK inhibitor (10 μmol/l) was added on the top of gel droplets. The culture medium was replaced every 2-4 days, and the ROCK inhibitor was maintained in the culture medium until day 7.

b) Passaging of Organoids and Cell Expansion

Depending on cell growth, organoid passaging was performed every 8-11 days by enzymatic (TrypLE) and mechanical dissociation of organoids embedded in Matrigel and the hydrogels of this invention to single cells. After gel and organoid dissociation, cells were counted and re-seeded in hydrogels of this invention or Matrigel at cell density of approximately 10000 cells per 20 μl droplet.

c) Experiments with Pre-Established Organoids

For experiments performed using pre-established organoids, organoids expanded in Matrigel for few passages were dissociated and re-seeded in prior art gels, hydrogels of this invention and Matrigel as described in b).

d) Organoid Forming Efficiency and Projected Total Number of Cells

Colony or organoid forming efficiency (OFE) was assessed by image analysis. OFE was defined as the ratio between formed organoids and the total number of objects (i.e. sum of single cells and organoids) detected in each image at a specific time point.

Figure 2:
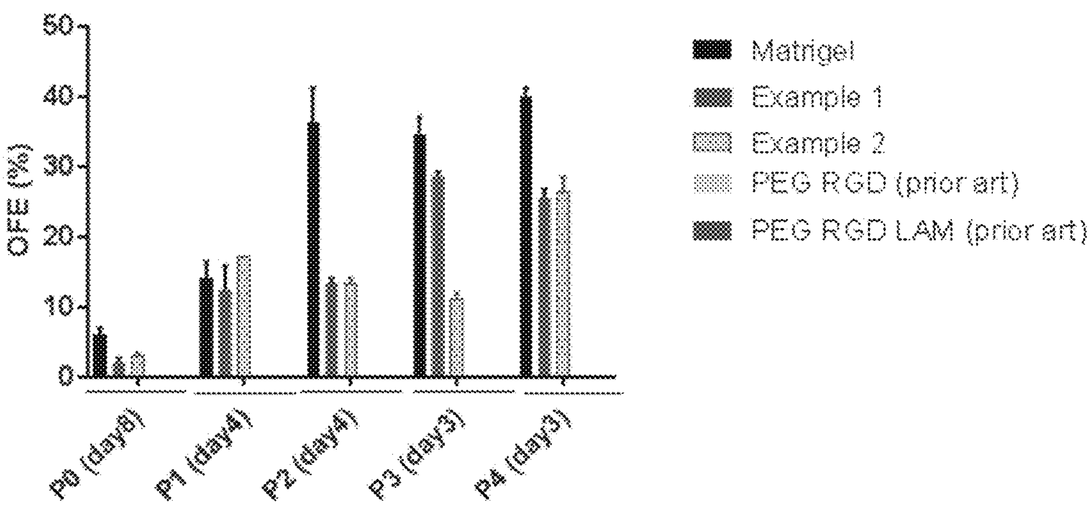
FIG. 2 shows the organoid forming efficiency (calculated at day indicated in bracket after seeding the cells in the three-dimensional matrix) of human intestinal organoids formed from a fresh human biopsy and cultured in vitro for 5 passages (P).
Figure 3:
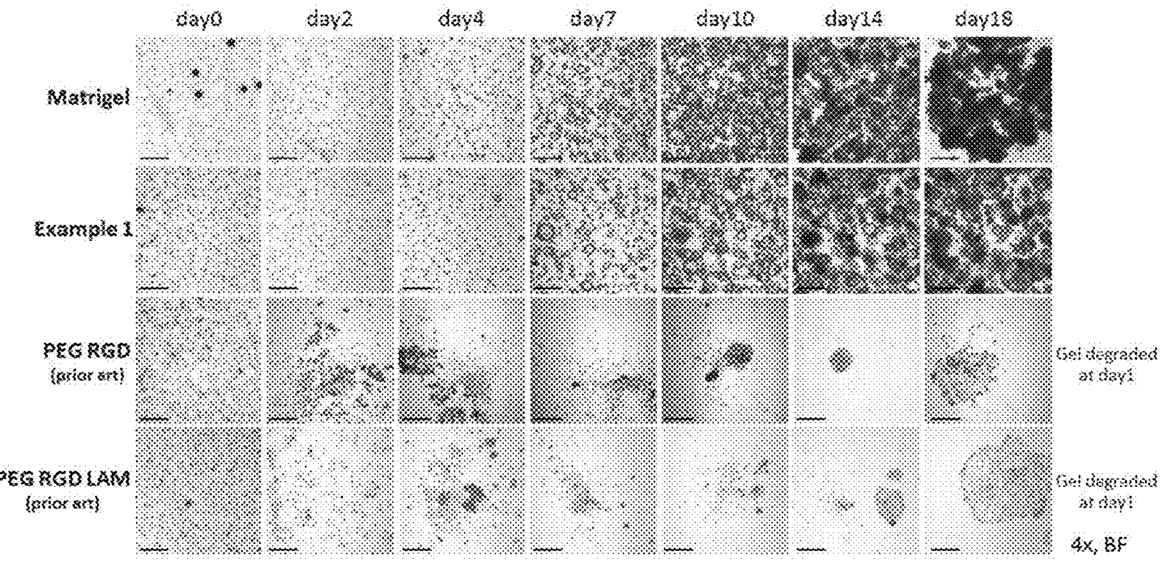
FIG. 3 shows the organoid formation from intestinal cells pre-cultured in Matrigel and grown for 18 days in a hydrogel according to example 1 (fully defined semi-synthetic), prior art gels (PEG RGD and PEG RGD LAM) or Matrigel, using the commercial culture medium IntestiCult™. Scale bar=500 μm.

From FIGS. 1 to 3 it can be seen that the hydrogels according to the present invention exhibit an organoid forming efficiency (OFE) that is comparable to the organoid forming efficiency (OFE) of Matrigel. Thus, the hydrogels of the present invention are at least equally suitable for organoid formation as the previously used standard Matrigel, but have the advantages discussed above, in particular the fully defined and especially fully synthetic composition resulting in clear advantages for regulatory approval.

In FIGS. 1 to 3, it can be seen that under the conditions described above in a) or b), the hydrogels of the present invention were stable and provided very good organoid forming efficiency (OFE), whereas the hydrogels from Gjorevski 2017 (designated therein as "PEG-RGD" and "PEG RGD LAM") degraded prematurely and consequently did not provide any suitable organoid forming efficiency (OFE).

The invention claimed is:

1. A biofunctional three-dimensional hydrogel suitable for the growth and the expansion of freshly isolated or frozen intestinal cells and the formation of intestinal organoids therefrom,
   wherein said hydrogel is the reaction product of at least one precursor molecule, which is a multi-arm PEG containing ethylenically unsaturated groups selected from the group consisting of vinylsulfone and acrylate moieties,
   a crosslinker molecule containing at least two nucleophilic groups capable of reacting with said ethylenically unsaturated groups of said multi-arm PEG in a Michael addition reaction, and
   at least one biofunctional ligand selected from the group consisting of natural laminins and recombinant laminin isoforms, characterized in that the crosslinker molecule comprises at least one RGD motif.

2. The hydrogel according to claim 1, wherein said multi-arm PEG is selected from the group consisting of a 4-arm and a 8-arm PEG.

3. The hydrogel according to claim 1, wherein said hydrogel has a shear modulus in the range of 50 to 1000 Pa.

4. The hydrogel according to claim 1,
   wherein said hydrogel is
   i. the reaction product of a 8-arm PEG vinylsulfone cross-linked with a peptide comprising at least two thiol groups and at least two RGD motifs, or
   ii. comprises the reaction product of a 8-arm PEG vinyl-sulfone crosslinked with a peptide comprising at least two thiol groups and at least two RGD motifs and/or the reaction product of a 8-arm PEG acrylate crosslinked with
   a peptide comprising at least two thiol groups and at least two RGD motifs.

5. The hydrogel according to according to claim 1, wherein the shear modulus of said hydrogel degrades over time.

6. The hydrogel according to according to claim 1, wherein said hydrogel does not comprise any moiety that is susceptible to enzymatic cleavage by cell-secreted proteases.

7. The hydrogel according to according to claim 1, wherein said crosslinker molecule is a peptide comprising at least two RGD motifs and at least two cysteine moieties.

8. The hydrogel according to claim 7, wherein said crosslinker molecule is AcGCREGRGDSPGGRGD-SPGERCG-$NH_2$.

9. Kit of parts for the growth and expansion of freshly isolated or frozen intestinal cells and the formation of intestinal organoids therefrom, comprising at least one precursor molecule, which is a multi-arm PEG containing ethylenically unsaturated groups selected from the group consisting of vinylsulfone and acrylate moieties,
   a crosslinker molecule containing at least two nucleophilic groups capable of reacting with said ethylenically unsaturated groups of said multi-arm PEG in a Michael addition reaction,
   wherein the crosslinker molecule comprises at least one RGD motif, and
   at least one biofunctional ligand selected from the group consisting of natural laminins and recombinant laminin isoforms, and
   a culture medium, wherein said culture medium comprises R-spondin 1 and Wnt3a.

10. Kit of parts according to claim 9, wherein said crosslinker molecule is a peptide comprising at least two RGD motifs and at least two cysteine moieties.

11. Kit of parts according to claim 9, wherein
   said precursor molecule is an 8-arm PEG vinylsulfone or a combination of an 8-arm PEG vinylsulfone and an 8-arm PEG acrylate.

12. A method of preparing a three-dimensional hydrogel according to claim 1, the method comprising the steps of
   a1) dispensing one or more different hydrogel precursor molecules, which is a multi-arm PEG containing ethylenically unsaturated groups selected from the group consisting of vinylsulfone and acrylate moieties, onto a substrate or into discrete volumes of a substrate, and adding to said hydrogel precursor molecules one or more crosslinker molecules containing at least two nucleophilic groups capable of reacting with said ethylenically unsaturated groups of said multi-arm PEG in a Michael addition reaction, wherein said crosslinker molecule comprises at least one RGD motif, and at least one biofunctional ligand selected from the group consisting of natural laminins and recombinant laminin isoforms; or a2) dispensing a resuspended unreacted powder onto a substrate or into discrete volumes of a substrate, wherein said unreacted powder comprises one or more different hydrogel precursor molecules, which is a multi-arm PEG containing ethylenically unsaturated groups selected from the group consisting of vinylsulfone and acrylate moieties, one or more crosslinker molecules containing at least two nucleophilic groups capable of reacting with said ethylenically unsaturated groups of said multi-arm PEG in a Michael addition reaction, wherein said crosslinker molecule comprises at least one RGD motif, and at least one biofunctional ligand selected from the group consisting of natural laminins and recombinant laminin isoforms;

b) adding freshly isolated or frozen intestinal cells from a biopsy of a human onto the substrate or into said discrete volumes of the substrate or into the hydrogel precursor formulations of a1) or a2) before addition onto the substrate or into said discrete volumes of the substrate; and c) crosslinking said hydrogel precursor molecules and said crosslinker molecules to form a hydrogel.

13. A method for the growth and expansion of freshly isolated or frozen intestinal cells, comprising the steps of:

a) de novo formation of organoids from freshly isolated or frozen human intestinal cells, using a kit of parts according to claim 9, preparing the three-dimensional hydrogel according to claim 1, incubating the three-dimensional hydrogel with said freshly isolated or frozen intestinal cells in the presence of the culture medium of said kit, b) growing, optionally passaging, and expanding of cells from the intestinal organoids from step a) using the kit of parts according to claim 9, c) optionally differentiating the organoids from step a), in the presence of a culture medium that induces cell differentiation, characterized that in said method only fully synthetic or fully defined semi-synthetic hydrogels are used.

14. The method according to claim 13, wherein in said method only fully defined semi-synthetic hydrogels are used which are self-degradable.

15. The method according to claim 13, wherein in said method only fully synthetic hydrogels are used which are self-degradable.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: synthetic construct

<400> SEQUENCE: 1

Arg Gly Asp Ser
1


<210> SEQ ID NO 2
<211> LENGTH: 5
<212> TYPE: PRT
<213> ORGANISM: Artificial Sequence
<220> FEATURE:
<223> OTHER INFORMATION: synthetic construct

<400> SEQUENCE: 2

Arg Gly Asp Ser Pro
1               5


<210> SEQ ID NO 3
<211> LENGTH: 6
<212> TYPE: PRT
<213> ORGANISM: Artificial Sequence
<220> FEATURE:
<223> OTHER INFORMATION: synthetic construct

<400> SEQUENCE: 3

Arg Gly Asp Ser Pro Gly
1               5


<210> SEQ ID NO 4
<211> LENGTH: 6
<212> TYPE: PRT
<213> ORGANISM: Artificial Sequence
<220> FEATURE:
<223> OTHER INFORMATION: synthetic construct

<400> SEQUENCE: 4

Arg Gly Asp Ser Pro Lys
1               5


<210> SEQ ID NO 5
<211> LENGTH: 5
<212> TYPE: PRT
<213> ORGANISM: Artificial Sequence
<220> FEATURE:
<223> OTHER INFORMATION: synthetic construct

<400> SEQUENCE: 5

Arg Gly Asp Thr Pro
1               5


<210> SEQ ID NO 6
```

-continued

```
<211> LENGTH: 10
<212> TYPE: PRT
<213> ORGANISM: Artificial Sequence
<220> FEATURE:
<223> OTHER INFORMATION: synthetic construct

<400> SEQUENCE: 6

Arg Gly Asp Ser Pro Ala Ser Ser Lys Pro
1               5                   10


<210> SEQ ID NO 7
<211> LENGTH: 22
<212> TYPE: PRT
<213> ORGANISM: Artificial Sequence
<220> FEATURE:
<223> OTHER INFORMATION: synthetic construct

<400> SEQUENCE: 7

Gly Cys Arg Glu Gly Arg Gly Asp Ser Pro Gly Gly Arg Gly Asp Ser
1               5                   10                  15

Pro Gly Glu Arg Cys Gly
            20
```